United States Patent [19]

Gallenkamp et al.

[11] Patent Number: 4,897,488

[45] Date of Patent: Jan. 30, 1990

[54] PROCESS FOR THE PREPARATION OF 2-CHLORO-5-METHYLPYRIDINE

[75] Inventors: Bernd Gallenkamp; Hans-Joachim Knops, both of Bayerwerk, Fed. Rep. of Germany

[73] Assignee: Bayer Aktiengesellschaft, Leverkusen, Fed. Rep. of Germany

[21] Appl. No.: 293,260

[22] Filed: Jan. 4, 1989

[30] Foreign Application Priority Data

Jan. 7, 1988 [DE]  Fed. Rep. of Germany ..... 38001799

[51] Int. Cl.$^4$ ........................................... C07D 213/26
[52] U.S. Cl. .................................... 546/345; 546/346
[58] Field of Search ................................ 546/345, 346

[56] References Cited

PUBLICATIONS

Abramovitch, Pyridine and its Derivatives, vol. 14, p. 112, Supplement Part Two, Wiley—Interscience, (1974), QD 401 A3 C.2.

*Primary Examiner*—Alan L. Rotman
*Attorney, Agent, or Firm*—Sprung Horn Kramer et al.

[57] ABSTRACT

In the preparation of 2-chloro-5-methylpyridine of the formula

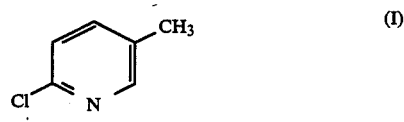

by reacting 3-methylpyridine 1-oxide with phosphorus oxychloride, the improvement which comprises carrying out the reaction in the presence of a basic organic nitrogen compound and in the presence of a diluent at a temperature between about −50° C. and +50° C.

10 Claims, No Drawings

PROCESS FOR THE PREPARATION OF 2-CHLORO-5-METHYLPYRIDINE

The invention relates to a novel process for the preparation of 2-chloro-5-methylpyridine.

It is known that 2-chloro-5-methylpyridine is obtained in addition to 2-chloro-3-methylpyridine, 4-chloro-3-methylpyridine and 3-chloro-5-methylpyridine by reacting 3-methylpyridine 1-oxide with phosphorus oxychloride (cf. Weissberger, Chemistry of Heterocyclic Compounds, Pyridine and its Derivatives, Vol. 14, Supplement, Part 2, p. 112). The main product of this reaction is 4-chloro-3-methylpyridine; the percentage of 2-chloro-5-methylpyridine is in general below 25%.

A novel process for the preparation of 2-chloro-5-methylpyridine of the formula (I)

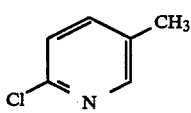

from 3-methylpyridine 1-oxide of the formula II)

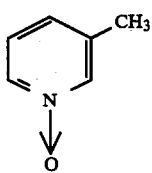

and phosphorus oxychloride has now been found, which is characterized in that the reaction is carried out in the presence of a basic organic nitrogen compound and in the presence of a diluent at temperatures between −50° C. and +50° C. and the reaction product is worked up in the usual manner.

It is surprising that, by the process according to the invention using basic organic nitrogen compounds, 2-chloro-5-methylpyridine can be obtained in a significantly higher yield than by the hitherto known method since by using phosphorus oxychloride and basic organic nitrogen compounds together, by-products from the reaction of these components with one another were more likely to occur.

Advantages of the process according to the invention, in addition to the good yield of the desired product, also reside in the fact that the proportion of isomeric by-products is significantly less than in the hitherto known synthetic method. Furthermore, the pure compound (I) can, if desired, be separated easily from the reaction product by conventional methods, for example by distillation.

Thus, the process according to the invention represents a valuable enrichment of industrial processes.

The course of the reaction in the process according to the invention can be outlined by the following equation:

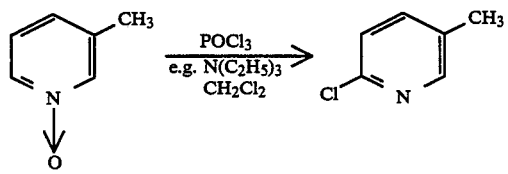

The starting materials for the process according to the invention—3-methylpyridine 1-oxide and phosphorus oxychloride—are known (cf. J. Am. Chem. Soc. 76 (1954), 1286-1291).

The process according to the invention is carried out in the presence of a basic nitrogen compound. Preferred basic organic nitrogen compounds are dialkylamines such as, for example, diethylamine, dipropylamine, diisopropylamine, dibutylamine, diisobutylamine and di-sec.butylamine, trialkylamines such as, for example, triethylamine, tripropylamine and tributylamine, dialkylcycloalkylamine such as, for example, dimethylcyclopentylamine, diethylcyclopentylamine, dimethylcyclohexylamine and dietylcyclohexylamine, dialkylaralkylamines such as, for example, dimethylbenzylamine and diethylbenzylamine and also dialkylarylamines such as, for example, dimethylaniline.

Diisopropylamine is particularly preferred as the basic organic nitrogen compound.

The process according to the invention is carried out in the presence of a diluent. Suitable diluents are practically all inert organic solvents. These include preferably halogenated or non-halogenated hydrocarbons such as pentane, hexane, heptane, octane, cyclohexane, methylcyclohexane, petroleum ether, benzine, ligroin, benzene, toluene, xylene, methylene chloride, chloroform, tetrachloromethane, 1,2-dichloroethane, chlorobenzene and dichlorobenzene, ethers such as diethyl ether, dipropyl ether, diisopropyl ether, dibutyl ether, methyl tert.butyl ether, glycol dimethyl ether, diglycol dimethyl ether, tetrahydrofuran and dioxane, ketones such as acetone, methyl ethyl ketone, diethyl ketone, methyl isopropyl ketone and methyl isobutyl ketone, esters such as methyl acetate, ethyl acetate, propyl acetate, butyl acetate and amyl acetate, nitriles such as acetonitrile and propionitrile, amides such as dimethylformamide, dimethylacetamide and N-methylpyrrolidone and also dimethyl sulphoxide and sulpholane.

Methylene chloride is particularly preferred as the diluent.

The reaction temperatures in the process according to the invention can vary within a relatively wide range. In general, the reaction is carried out at temperatures between −50° C. and +50° C., preferably at temperatures between −20° C. and +20° C.

The process according to the invention is in general carried out at atmospheric pressure. However, it is also possible to work at elevated or reduced pressure between 0.1 and 10 bar.

The process according to the invention is carried out by using in general between 1 and 10 moles, preferably between 1.5 and 2.5 moles, of phosphorus oxychloride and also between 1 and 10 moles, preferably between 1.5 and 2.5 moles, of the basic organic nitrogen compound per mole of 3-methylpyridine 1-oxide of the formula (II). The use of approximately 2 moles each of phosphorus oxychloride and nitrogen compound per mole of 3-methylpyridine 1-oxide is particularly preferred.

In a preferred embodiment of the process according to the invention, the 3-methylpyridine 1-oxide is initially introduced in a diluent and, with stirring and cooling, the phosphorus oxychloride, dissolved in a diluent, and the basic organic nitrogen compound, also dissolved in a diluent, are metered in at the same time ("simultaneously", "parallel"), the phosphorus oxychloride being preferably added a short time ahead so that between 5% and 20% of the phosphorus oxychloride is already present in the reaction mixture by the time the addition of the basic organic nitrogen compound is started. The entire reaction mixture is stirred until the reaction is completed.

The work-up can be carried out in a conventional manner. Preferably, water is added to the reaction mixture with stirring and cooling, the organic solvent is removed—for example by distillation—the aqueous phase is adjusted to a pH of 6 with an aqueous alkali metal or alkaline earth metal hydroxide solution such as, for example, sodium hydroxide solution, and the reaction product is largely removed from this mixture by steam distillation. The organic portion of the steam distillate essentially contains the product of the formula (I).

The preparation of the compound of the formula (I) in pure form from the organic portion of the steam distillate can be carried out by conventional methods, for example by fine distillation in a packed column. At a pressure of 3.3 mb, the compound of the formula (I) has a boiling point of 56° C. The total yield in the preparation of pure product (I) is 55–62% of theory, starting from 3-methylpyridine 1-oxide.

The 2-chloro-5-methylpyridine preparable by the process according to the invention is known as an intermediate for pharmaceuticals (cf. German Offenlegungsschrift 2,812,585).

Furthermore, 2-chloro-5-methylpyridine can be used as an intermediate for insecticides.

EXAMPLE 1

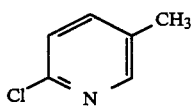

10% of a solution of 76.7 g (0.5 mole) of phosphorus oxychloride in 50 ml of methylene chloride is added dropwise to 27.3 g (0.25 mole) of 3-methylpyridine 1-oxide in 400 ml of methylene chloride at about −10° C. The remaining 90% of this solution is then added dropwise simultaneously with a mixture of 50.6 g (0.5 mole) of diisopropylamine in 50 ml of methylene chloride over a period of 3 hours at −10° C. Stirring is continued for about 2½ hours at this temperature. 75 ml of water are then added with cooling, the methylene chloride is distilled off, the reaction mixture is brought to a pH of 6 with about 290 ml of 20% strength sodium hydroxide solution and subjected to steam distillation.

Usual work-up gives 20.5 g of a product mixture which has the following composition according to the gas chromatogram (by the 100% method):

81% of 2-chloro-5-methylpyridine,
15% of 2-chloro-3-methylpyridine, and
1% of β-picoline.

It will be appreciated that the instant specification and claims are set forth by way of illustration and not limitation, and that various modifications and changes may be made without departing from the spirit and scope of the present invention.

What is claimed is:

1. In the preparation of 2-chloro-5-methylpyridine of the formula

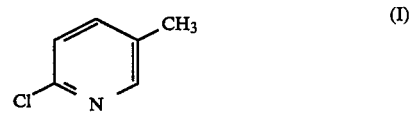

by reacting 3-methylpyridine 1-oxide with phosphorus oxychloride, the improvement which comprises carrying out the reaction in the presence of a basic organic nitrogen compound and in the presence of a diluent at a temperature between about −50° C. and +50° C.

2. The process according to claim 1, wherein the basic organic nitrogen compound is selected from the group consisting of a dialkylamine, a trialkylamine, a dialkylcycloalkylamine, a dialkylaralkylamine and a dialkylarylamine.

3. The process according to claim 1, wherein the basic organic nitrogen compound is diisopropylamine.

4. The process according to claim 1, wherein the diluent is an inert organic solvent.

5. The process according to claim 1, wherein the diluent is methylene chloride.

6. The process according to claim 1, wherein the reaction is carried out at about −20° C. to +20° C.

7. The process according to claim 1, wherein about 1 to 10 moles of the basic organic nitrogen compound are used per mole of 3-methylpyridine 1-oxide.

8. The process according to claim 1, wherein the reaction mixture formed in the reaction is subjected to steam distillation.

9. The process according to claim 8, wherein the residue of the steam distillation is subjected to distillation to distill off the pure compound (I).

10. The process according to claim 8, wherein the basic organic nitrogen compound is diisopropylamine, the diluent is methylene chloride, the reaction is carried out at about −20° C. to +20° C. and about 1 to 10 moles of the basic organic nitrogen compound are used per mole of 3-methylpyridine 1-oxide.

* * * * *